United States Patent [19]
Xun et al.

[11] Patent Number: 5,837,504
[45] Date of Patent: Nov. 17, 1998

[54] METHOD OF MAKING L-DOPA FROM L-TYROSINE

[75] Inventors: Luying Xun, Richland, Wash.; Jang Young Lee, Taejon, Rep. of Korea

[73] Assignees: Battelle Memorial Institute, Richland; The Washington State University Research Foundation, Pullman, both of Wash.

[21] Appl. No.: 34,987

[22] Filed: Mar. 4, 1998

[51] Int. Cl.⁶ .................................................. C12P 13/22
[52] U.S. Cl. .......................... 435/108; 435/189; 435/191; 435/252.33; 435/252.4; 435/320.1
[58] Field of Search ................................ 435/108, 252.8, 435/191, 189, 252.33, 252.4, 320.1

[56] References Cited

U.S. PATENT DOCUMENTS

| | | | |
|---|---|---|---|
| 3,671,397 | 6/1972 | Sih | 435/108 |
| 3,767,528 | 10/1973 | Nagasaki et al. | 435/108 |
| 5,338,672 | 8/1994 | Tsuchida et al. | 435/108 |

*Primary Examiner*—Herbert J. Lilling
*Attorney, Agent, or Firm*—Paul W. Zimmerman

[57] ABSTRACT

The invention is a method of making a L-dopa from L-tyrosine in the presence of an enzyme catalyst and oxygen. By starting with L-tyrosine, no variant of the L-dopa is produced and the L-dopa is stable in the presence of the enzyme catalyst. In other words, the reaction favors the L-dopa and is not reversible.

16 Claims, 3 Drawing Sheets

METHOD OF MAKING L-DOPA FROM L-TYROSINE

This invention was made with Government support under Contract DE-AC06-76RLO 1830 awarded by the U.S. Department of Energy. The Government has certain rights in the invention.

FIELD OF THE INVENTION

The present invention relates generally to a method for producing L-dopa (L-dihydroxyphenylalanine) from L-tyrosine. More specifically, 4-hydroxyphenylacetate 3-hydroxylase (HPAH) (also called 4-hydroxyphenylacetate 3-monooxygenase), an enzyme catalyst, oxidizes the L-tyrosine to the L-dopa with the co-consumption of molecular oxygen ($O_2$) and reduced beta-nicotinamide adenine dinucleotide (NADH).

BACKGROUND OF THE INVENTION

The compound L-dopa is used as a drug to treat parkinson's disease. In the United States, the compound was previously sold as a mixture of L-dopa with D-dopa (only the L-dopa is active). L-Dopa is now sold as a mixture of carbidopa and L-dopa wherein the carbidopa is an inhibitor preventing conversion of L-dopa to dopamine in blood. L-dopa has a total market volume of about $60 million per year. Worldwide, the market is estimated at about $1.1 billion.

L-dopa and D-dopa are isomers of the same chemical compound.

L-dopa is presently produced by chemical synthesis by one of two following methods. One method developed by H. Enei and H. Yamada, 1986, 3,4-dihydroxyphenylalanine, p.280–285, In K. Aida et al. (Ed), Progress in industrial microbiology, vol. 24: biotechnology of amino acid production, Elsevier, Amsterdam and described by F. Foor, N Morin, and K A Bostian, PRODUCTION OF L-DIHYDROXYPHENYLALANINE IN *ESCHERICHIA COLI* WITH THE TYROSINE PHENOL-LYASE GENE CLONED FROM *ERWINIA HERBICOLA*, Applied and Environmental Microbiology, Sept. 1993, p. 3070–3075 starts with catechol and requires pyruvate and ammonium in the presence of an enzyme catalyst. This process results in a mixture of L-dopa and the beginning substrates thereby requiring subsequent separation of the L-dopa from the catechol. Moreover, in this catechol method, the L-dopa producing reaction is reversible providing yields of L-dopa of less than 50% because the reaction favors catechol. Another disadvantage is that catechol is a toxic compound. Because the pyruvate is expensive, the yield is low, and separation is required the cost of obtaining L-dopa from this process is high.

A second method of making L-dopa is described by S. CHTTOPADHYAY AND D. ARAIL, PRODUCTION OF L-DOPA BY *ASPERGILLUS TERREUS*, FEMS MICROBIOLOGY LETTER, 1990, vol. 72, p. 195–200. In this second method, the fungus *Aspergullus terreus* produces tyrosine hydroxylase. Because of the tendency of tyrosine hydroxylase to oxidze L-dopa in addition to catalyzing the reaction producing L-dopa, sophisticated reaction control is required to avoid the oxidation of the L-dopa. Hence the yield of L-dopa from this second process is quite low, less than 1 mM, resulting in a high cost to produce L-dopa.

Accordingly, there is a need for a method of making L-dopa with high yield, resulting in lower cost.

SUMMARY OF THE INVENTION

The invention is a method of producing or making L-dopa from L-tyrosine in the presence of an enzyme catalyst and oxygen. By starting with L-tyrosine, no variant of the L-dopa is produced and the L-dopa is stable in the presence of the enzyme catalyst. The reaction favors the formation of the L-dopa and is irreversible. The method converts L-tyrosine to L-dopa by 4-hydroxyphenylacetate 3-hydroxylase (HPAH) (also called 4-hydroxyphenylacetate 3-monooxygenase), an enzyme catalyst, with the co-consumption of oxygen ($O_2$) and -nicotinamide adenine dinucleotide, reduced form (NADH). Using an *Escherichia coli* host harboring the genes encoding the enzyme, L-tyrosine was successfully converted to L-dopa. The bacterial cells provide the enzyme with NADH for the oxidation of L-tyrosine to L-dopa. The bacterium host is simply the presently least cost (preferred) method of supplying or providing the NADH. The present invention contemplates use of NADH independently from the bacterial host as well where there may be special circumstances where it is necessary or useful to omit the bacterium host even though commercially available NADH is more expensive.

It is, therefore, an object of the present invention to provide a method of making L-dopa from L-tyrosine.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(s)

According to the present invention, a method of making L-dopa from L-tyrosine, has the steps of:
 (a) oxidizing the L-tyrosine in the presence of HPAH; and
 (b) co-consuming molecular oxygen and NADH; thereby
 (c) producing the L-dopa.

In a preferred embodiment, the NADH is obtained from a bacterium host. More specifically, the L-dopa may be obtained by
 (a) preparing a cell suspension with a plurality of bacteria having HPAH activity;
 (b) adding the L-tyrosine and a substrate to the cell suspension and making a reactive mixture; and
 (c) incubating the reactive mixture for a time to produce the L-dopa.

Figure 1:
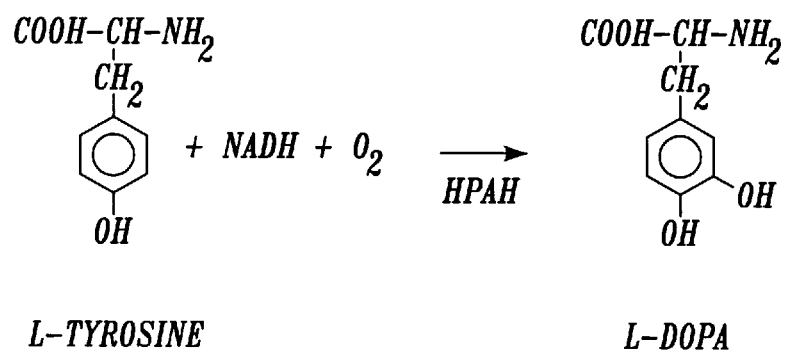
FIG. 1 is a schematic of the enzymatic reaction of L-tyrosine to L-dopa according to the method of the present invention.

The reaction that occurs during the incubation (step c) is shown in FIG. 1.

To the extent that purification or separation of the L-dopa from the reacted mixture is needed, the method may further include a step of separating the L-dopa from the reacted mixture.

The bacteria or bacterium possesses HPAH activity and includes but is not limited to *E. coli* W, *E. coli* S17λ.pir carrying plasmid pAJ224 (strain AJ224), *E. coli* DH1 carrying plasmid pAJ221 (strain AJ221), or combinations thereof. Alternatively, HPAH may be cloned into other host strains.

Although strain AJ224 has higher specific activity compared to strain AJ221 and *E. coli* W, strain AJ224 requires isopropyl-thio-galactopyranoside (IPTG) as an inducer which is an expensive compound. It is therefore preferred to use strain AJ221 in combination with a substrate that is used by the cells to generate NADH. The substrate may be selected from the group of small organic compounds, hydrogen and combinations thereof. Small organic compounds include but are not limited to organic acids, for example pyruvic acid, lactic acid, acetic acid, glutamic acid and combinations thereof, alcohols, for example glycerol, ethanol and combinations thereof, and combinations of organic acids and alcohols. Glycerol is preferred.

EXAMPLE 1

An experiment was conducted to demonstrate making L-dopa from L-tyrosine.

*E. coli* W showing HAPH activity was grown in a substrate of 50 ml Luria-Bertani (LB) medium (10 g trypton, 10 g sodium chloride, 5 g yeast extract per liter of distilled water) to late logarithmic phase. 2 g/L p-hydroxyphenylacetate was added to the LB medium to induce the enzyme HAPH. Bacterial cells were harvested by centrifugation at 5,000×g for 20 minutes and washed twice with Tris-HCL buffer (20 mM, pH 8.0). Harvested cells were resuspended in 25 ml Tris-HCL buffer (100 mM, pH 8.0). L-tyrosine was added to the resuspended cells to a concentration of 1 mM forming a reactive resuspension.

The reactive resuspension was incubated at 37° C. with mild shaking (120 rpm) for 2 hours. The reaction was stopped by centrifugation at 10,000×g for 5 min and removing bacterial cells forming a clarified solution containing the L-dopa.

The clarified solution was analyzed by the colorimetric assay (Nair and Vaidhyanathan, 1964, A COLORIMETRIC METHOD FOR DETERMINATION OF PYROCATECHOL AND RELATED SUBSTRATES, Anal. Biochem. 7:315–321) confirming formation of dihydroxy derivative of L-tyrosine.

The clarified solution was further analyzed by high pressure liquid chromatography (HPLC) to confirm that the dihydroxy derivative was L-dopa. A Nova-Pak C18 column (3.9×150 mm) was used with an eluting mobile phase of 11 mM of phosphoric acid (Solvent A) and acetonitrile (Solvent B) at ambient temperature. The HPLC analysis was performed with a gradient elution condition (100% solvent A, 0% solvent B for 5 min, changed to 30% solvent A, 70% solvent B for 5 min, maintained at 30% solvent A, 70% solvent B for 5 min, changed to 0% solvent A, 100% solvent B for 0.5 min, and maintained 0% solvent A, 100% solvent B for 0.5 min) at a constant flow rate of 1 ml/min. Detection was done at variable wavelengths from 250–350 nm. The dihydroxy derivative eluted at retention time of 3.5 min which matches the retention time of elution for L-dopa.

The dihydroxy derivative was further analyzed by UV absorption spectrum showing a peak maxima at 280 nm, identical to the peak maxima of L-dopa.

EXAMPLE 2

An experiment was conducted to demonstrate that the enzyme HPAH was necessary to produce the L-dopa.

Two colonies of bacteria were used, (1) *E. coli* DH1 (strain AJ221) containing cloned HPAH genes in the plasmid ACYC184, and (2) *E. coli* DH1 without the HPAH genes.

Both colonies were grown, reacted and analyzed as described in Example 1. Analysis showed that the L-tyrosine was converted to L-dopa for the first colony (*E. coli* DH1 containing a cloned HPAH gene) whereas no consumption or conversion of L-tyrosine occurred during incubation of the second colony (*E. coli* DH1 without an HPAH gene).

EXAMPLE 3

An experiment was conducted to demonstrate an alternative method compared to Example 1.

A colony of bacteria of *E. coli* S17λpir (strain AJ224) containing a cloned HPAH gene in the plasmid pCNB5 was grown. The expression of HPAH gene in pCNB5 is controlled by Ptrc promoter originated from the plasmid rather than its own promoter thereby overexpressing the HPAH genes.

Strain AJ224 was grown in 50 ml LB medium. 1 mM isopropyl-thio-galactopyranoside (IPTG) was added for induction when the optical density at 660 nm reach 0.8. After 3 hour induction, cells were harvested by centrifugation at 5,000 g for 20 min and washed twice with Tris-HCL buffer (20 mM, pH 8.0). Harvested cells were resuspended in 25 ml Tris-HCL buffer (100 mM, pH 8.0) and L-tyrosine was added to a concentration of 3 mM making a reactive mixture.

The reactive mixture was incubated at 37° C. with mild shaking (120 rpm) for 1 hour. The reaction was stopped by centrifugation at 10,000×g for 5 min removing cells and producing a clarified solution.

The clarified solution was analyzed as in Example 1. Results of the analyses showed that L-tyrosine was converted to L-dopa at a rate of 44 μM/min with a final concentration of L-dopa of 2.66 mM and a conversion yield of 88.7%.

EXAMPLE 4

An experiment was conducted to demonstrate use of glycerol to maintain reducing potential of cells for strain AJ221.

A cell suspension of AJ221 having HPAH activity was prepared as in Example 2. The stock solution of L-tyrosine was made in 1N NaOH to a concentration of 750 mM. 500 ul of the stock solution was added to 25 ml of the cell suspension to a final concentration of 15 mM. Concentrations of L-tyrosine in excess of 15 mM resulted in precipitation of insoluble particles. Glycerol was added to a final concentration of 5 vol %.

A control cell suspension without glycerol was also prepared.

The two suspensions were incubated as in Example 2. Samples were removed from the incubating suspensions, acidified with 15 μl of 5N HCL, centrifuged and 10,000×g for 5 min and stored at 4° C. for analysis.

Figure 2:
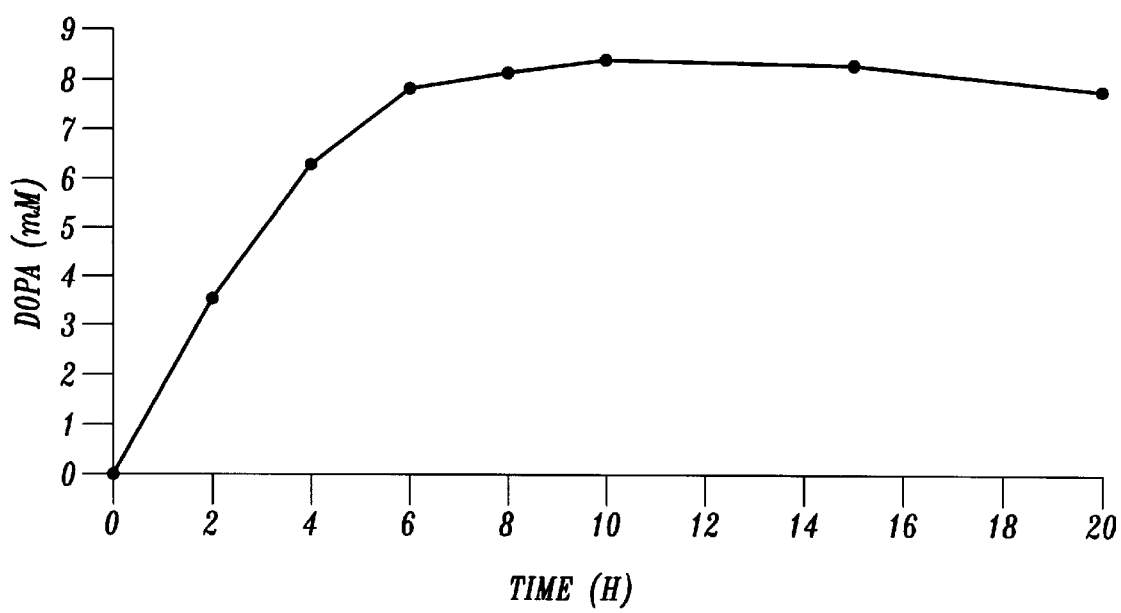
FIG. 2 is a graph of L-dopa concentration versus time in a batch reaction.

Samples were analyzed according to Example 1 and results are shown in FIG. 2. The L-dopa rapidly accumulated up to about 6 hours of incubation. No further L-dopa production was observed after 6 hours of incubation. In the control, a black pigment was observed indicative of autooxidation of L-dopa, whereas in the glycerol containing suspension, no black pigment formed. The final concentration of L-dopa from the glycerol containing suspension was 8.2 mM.

EXAMPLE 5

An experiment was conducted to demonstrate staged addition of L-tyrosine or fed batch process.

Figure 3:
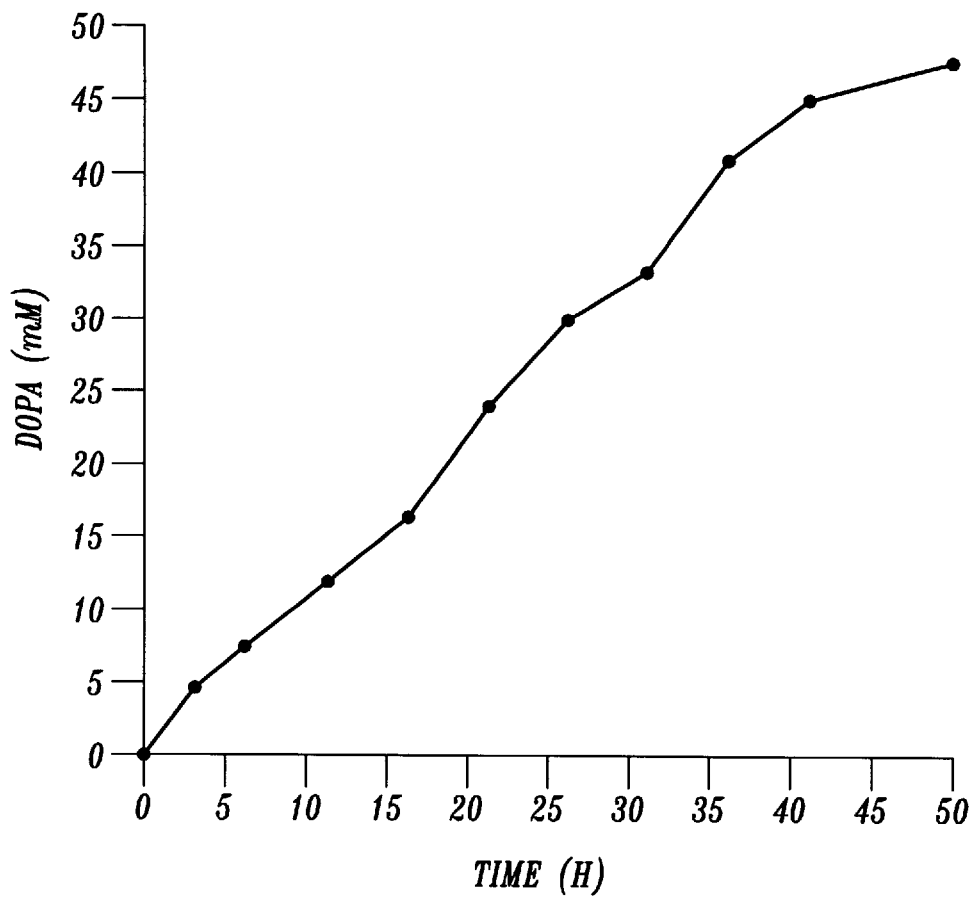
FIG. 3 is a graph of L-dopa concentration versus time in a fed batch reaction.

A cell suspension of strain AJ221 having HPAH activity was prepared as in Example 2. Glycerol was added to a concentration of 5 vol %. L-tyrosine was added to an initial concentration of 15 mM. After 6 hours of incubation, aliquots of 15 mM of L-tyrosine were added 4 times every 10 hours. Samples were removed, acidified, stored then analyzed as in Example 4. L-dopa accumulated to a final concentration of 48 mM after about 50 hours of incubation (FIG. 3).

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of making L-dopa from L-tyrosine, comprising the steps of:
   (a) oxidizing said L-tyrosine in the presence of HPAH; and
   (b) co-consuming molecular oxygen and NADH; thereby
   (c) producing a reacted mixture containing said L-dopa.

2. The method as recited in claim 1, further comprising the step of separating the L-dopa from the reacted mixture.

3. The method as recited in claim 1, wherein said HPAH is provided by a plurality of bacteria having HPAH activity.

4. The method as recited in claim 3, wherein said plurality of bacteria is provided by
   (a) preparing a cell suspension.

5. The method as recited in claim 3, wherein said plurality of bacteria is selected from the group consisting of *E. coli* W, *E. coli* S17λpir carrying plasmid pAJ224 (strain AJ224), *E. coli* DH1 carrying plasmid pAJ221 (strain AJ221).

6. The method as recited in claim 4, wherein said oxidizing is by
   (a) adding said L-tyrosine and a substrate to the cell suspension to generate NADH and making a reactive mixture; and
   (b) incubating the reactive mixture for a time with co-consumption of molecular oxygen and said NADH to produce the L-dopa.

7. The method as recited in claim 6, wherein said substrate is selected from the group consisting of small organic compounds, hydrogen and combinations thereof.

8. The method as recited in claim 7, wherein said small organic compounds are selected from the group consisting of organic acids, alcohols and combinations thereof.

9. The method as recited in claim 8, wherein said organic acids are selected from the group consisting of pyruvic acid, lactic acid, acetic acid, glutamic acid and combinations thereof.

10. The method as recited in claim 8, wherein said alcohols are selected from the group consisting of glycerol, ethanol and combinations thereof.

11. A method of making L-dopa from L-tyrosine, comprising the steps of:
    (a) preparing a cell suspension with a plurality of bacteria having HAPH activity;
    (b) adding said L-tyrosine and a substrate to the cell suspension to generate NADH and making a reactive mixture; and
    (c) incubating the reactive mixture for a time in the presence of the HPAH with co-consumption of molecular oxygen and said NADH to obtain the L-dopa.

12. The method as recited in claim 11, wherein said substrate is selected from the group consisting of small organic compounds, hydrogen and combinations thereof.

13. The method as recited in claim 11, wherein said small organic compounds are selected from the group consisting of organic acids, alcohols and combinations thereof.

14. The method as recited in claim 13, wherein said organic acids are selected from the group consisting of pyruvic acid, lactic acid, acetic acid, glutamic acid and combinations thereof.

15. The method as recited in claim 13, wherein said alcohols are selected from the group consisting of glycerol, ethanol and combinations thereof.

16. The method as recited in claim 11, wherein said plurality of bacteria is selected from the group consisting of *E. coli* W, *E. coli* S17λpir carrying plasmid pAJ224 (strain AJ224), *E. coli* DH1 carrying plasmid pAJ221 (strain AJ221).

* * * * *